US00PP09808P

United States Patent [19]

van der Meer

[11] Patent Number: Plant 9,808

[45] Date of Patent: Feb. 18, 1997

[54] HYBRID TEA ROSE PLANT NAMED 'SELGALLIA'

[75] Inventor: Peter J. A. van der Meer, Oceanside, Calif.

[73] Assignee: Terra Nigra Holding B.V., PA De Kwakel, Netherlands

[21] Appl. No.: 591,388

[22] Filed: Jan. 25, 1996

[51] Int. Cl.[6] ..... A01H 5/00

[52] U.S. Cl. ..... Plt./18

[58] Field of Search ..... Plt./11, 16, 18

*Primary Examiner*—Howard J. Locker

[57] ABSTRACT

A new rose variety of the Hybrid Tea class, characterized by its continuous good production of apricot colored flowers having good bud size in relation to the size of the stem, said flowers being borne singly on upright stems on a bush of medium height (100–130 cm.), and that is especially well suited for growing in mountainous countries (typical growth conditions such as light intensity, day length, and seasonal effects), such as in Latin America. The cultivar is grown mainly under cover.

2 Drawing Sheets

BACKGROUND OF THE INVENTION

The present invention relates to a new and distinct variety of rose plant of the Hybrid Tea class, which was discovered by me as being a naturally occurring mutant of the variety 'Marjan'.

The primary objective of this breeding was to obtain a new large type rose having good bud size in relation to its stem, in different colors. Among the novel characteristics possessed by the new variety which distinguish it from its parent and all other varieties of which I am aware are:

(1) The apricot color of the flower.

The other distinctive characteristics, which distinguish it from all other varieties of which I am aware, already possessed by its parent are retained:

(2) A very large flower and flower bud.

(3) Rapid flowering cycles.

(4) Suitabiliy for growing in Latin America.

(5) Good bud size in relation to its stem length.

Asexual reproduction of the new rose variety by cutting and grafting using *R. canina* 'Inermis' as rootstock, as performed in a greenhouse in Quito, Ecuador, shows that the aforementioned characteristics and distinctions come true to form and are established and transmitted through succeeding propagations.

BRIEF DESCRIPTION OF THE DRAWINGS

The new variety of rose plant is illustrated by the accompanying photographic illustrations, of which:

Sheet 1 shows a full face view of the flower; and

Sheet 2 shows typical specimens of the vegetative growth and flowers of the new variety in different stages of development and as depicted in color as nearly true as it reasonably possible to make the same in color illustrations of this character.

The following is a detailed description of this new variety, with color terminology in accordance with The Royal Horticultural Society Colour Chart (R.H.S.C.C.). The terminology used in the color description herein refers to plate numbers in the aforementioned color chart e.g. "55C" is plate "55C" of The Royal Horticultural Society Colour Chart.

Origin: Mutant of 'Marjan', that has occurred naturally as a branch.

Classification:

*Commercial.*—Hybrid Tea.

BOTANICAL DESCRIPTION OF THE PLANT

Flower (Observations made from specimens grown in a greenhouse in Quito, Ecuador)

Blooming habit of 'Selgallia': Almost continuous.

Time of beginning of flowering: Early.

A. Bud:

(1) *Size.*—Large. Diameter 4.0–4.5 cm. Length 5.5–6.0 cm.

(2) *Form.*—Egg shaped (long); is not affected by wet or hot weather.

(3) *Color.*—When the sepals first divide, the color of the outside is 29D.

(4) *Sepals.*—Length: 40 to 50 mm. Slightly branched, curl back when petals start to unfurl. Color: inside: 143C outside: 143C flushed with 178A.

(5) *Calyx.*—Color: 144A. Shape: funnel. Size: long. Aspect: smooth. Odor when rubbed: a little; Quality: spicy.

(6) *Rate of opening.*—Normal to rapid.

(7) *Peduncle.*—Length: long, 9 to 10 cm. Aspect: glandular with some small prickles. Strength: medium. Color: 144A touched with 174B.

(8) *Opening.*—Opens up well; is not affected by adverse weather.

B. Bloom:

(1 *Size.*—Large; when fully expanded about 11 cm in diameter with a depth of about 4.5 cm.

(2) *Borne.*—Single.

(3) *Stems.*—Length: long. Strength: strong.

(4) *Form (when first open).*—Round, center irregular. Permanence: will flatten when aging.

(5) *Petalage.*—Number of petals: average 35.

(6) *Color.*—Center of flower: 38C. Outer petals: 38D. Base of petals: 8C, with a spot at the base of 8B. Inside of petals: 38B. Reverse of petals: 38D. General tonality: peach/apricot 38B.

(7) *Discoloration.*—General tonality 38B fading to 38D.

C. Petals:

(1) *Texture.*—Soft; is not affected by wet or hot weather.

(2) *Appearance.*—Inside shiny. Outside: satiny.
(3) *Form.*—Obovate.
(4) *Arrangement.*—Outer petals regular, inner petals irregular.
(5) *Petaloids in center.*—Number: average 2. Size: 1 cm. Color: base 14B, middle and marginal zone between 29B and 28C.
(6) *Persistence.*—Drop off cleanly.
(7) *Fragrance.*—Medium; Honey-like scent.
(8) *Lasting quality.*—As cutflower: 10 days. On the plant: good.

Reproductive Organs

A. Stamens:
(1) *Arrangement.*—Around styles, differing in height.
(2) *Number.*—Average close to 120.
(3) *Length.*—6 to 12 mm.
(4) *Anthers.*—Size: medium, 3 to 4 mm. Color: 11A.
(5) *Filaments.*—Length: different, 6 to 12 mm. Color: base of anthers 13A, lower filament 13C.
(6) *Pollen.*—Color: 17C.

B. Pistils:
(1) *Styles.*—Number: average close to 120. Length: 10 to 14 mm. Color: Base: 11D. Top 52B.
(2) *Stigmas.*—Color: 11A.
(3) *Fruit.*—Fertility: Unknown. Fruit/hips: Shape: pitcher.

Plant

A. Form: Greenhouse rose.
B. Growth: Vigorous upright.
C. Height: Medium, 100 to 130 cm.
D. Foliage: Compound of 3 or 5 leaflets. Average 7 to 8 compound leaves on bloom stem, 9 to 11 on main canes.
(1) *Size.*—Small; 9 to 11 cm.
(2) *Quantity.*—Average; stem covering.
(3 ) *Color.*—New foliage: upper side: 139A. under side: 138B. Old foliage: upper side: 139A. under side: 137D.
(3) *Texture.*—upper side: leathery, glossy. Underside: smooth, dull.
(4) *Terminal leaflet.*—Shape: oval, base rounded. Size: small. Length 70 to 75 mm. Diameter 50 to 55 m. Length petiole 18 to 25 mm.
(5) *Ribs and veins.*—When young, veins with anthocyanin coloration.
(6) *Rachis.*—Upper side: few hairs and few short needles. Lower side: 1 mm sized small prickles, zero to 2 per compound leaf.
(7) *Margin type.*—Medium serrate, 3 points/cm, 3 mm peak.
(8) *Stipules.*—Length: average 10 to 20 mm, auricle to 7 mm. Texture: slightly hairy. Color: 137B.

E. Resistance to diseases: Average.

F. Wood:
(1) *New wood.*—Color: green/bronze, between 147A and 148A. Bark: smooth.
(2) *Old wood.*—Color: green. Bark: smooth.

G. Thorns:
(1) *Quantity.*—Medium.
(2) *Form.*—Upper side concave, lower side deep concave.
(3) *Length.*—Medium, 7 to 9 mm.
(4) *Hooked.*—Downward.
(5) *Color* (*when young*).—Light brownish, 199B.
(6) *Position.*—Irregular.

H. Prickles:
*Quantity.*—On peduncle: none. On rachis: some, very small.

I. Short needles:
*Quantity.*—On rachis and peduncle small sized and average presence.

I claim:

1. A new and distinct variety of rose plant of the Hybrid Tea class, substantially as herein shown and described characterized particularly as to novelty by its large apricot flowers, borne singly on uprigh stems with good bud size in relation to its stem size, especially suitable for growing in Latin America.

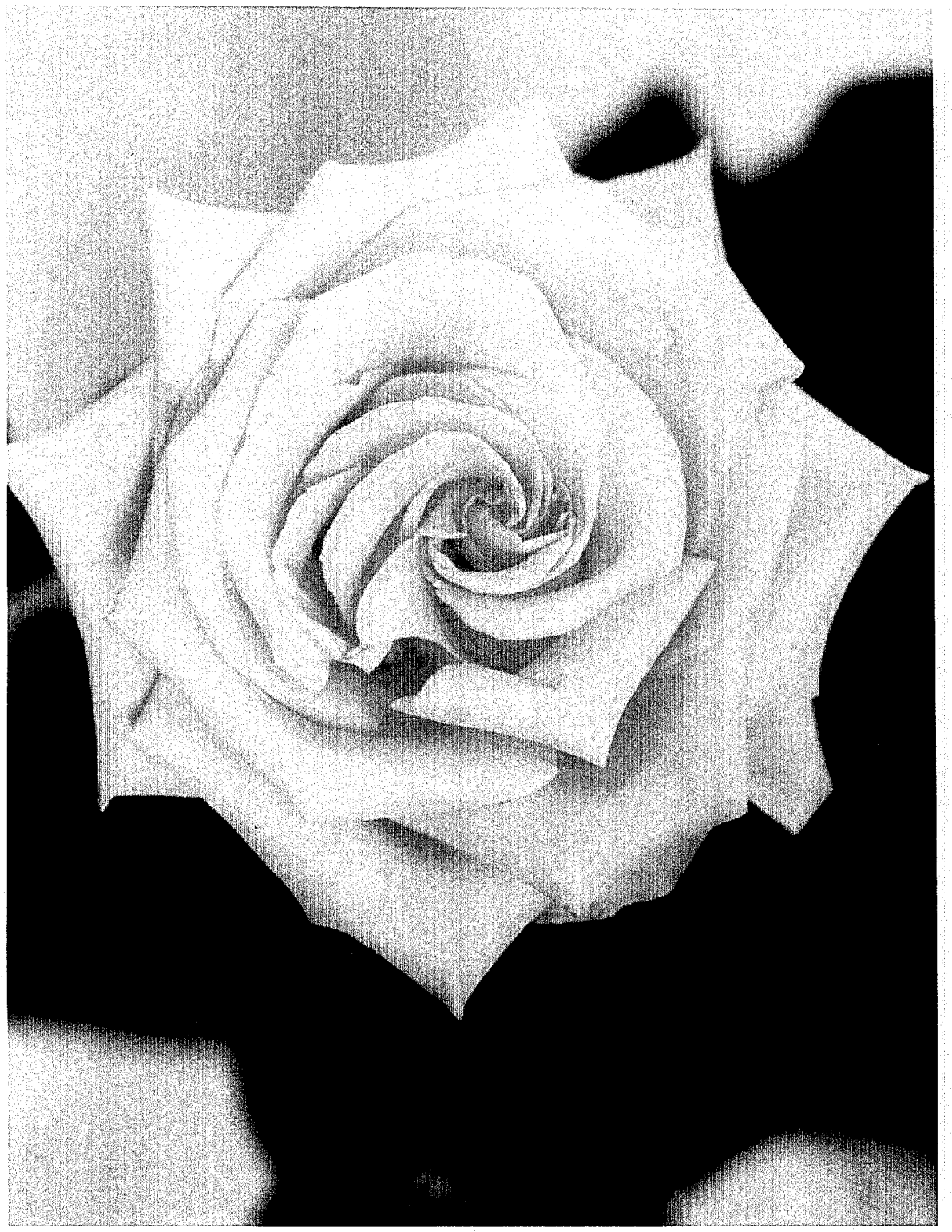

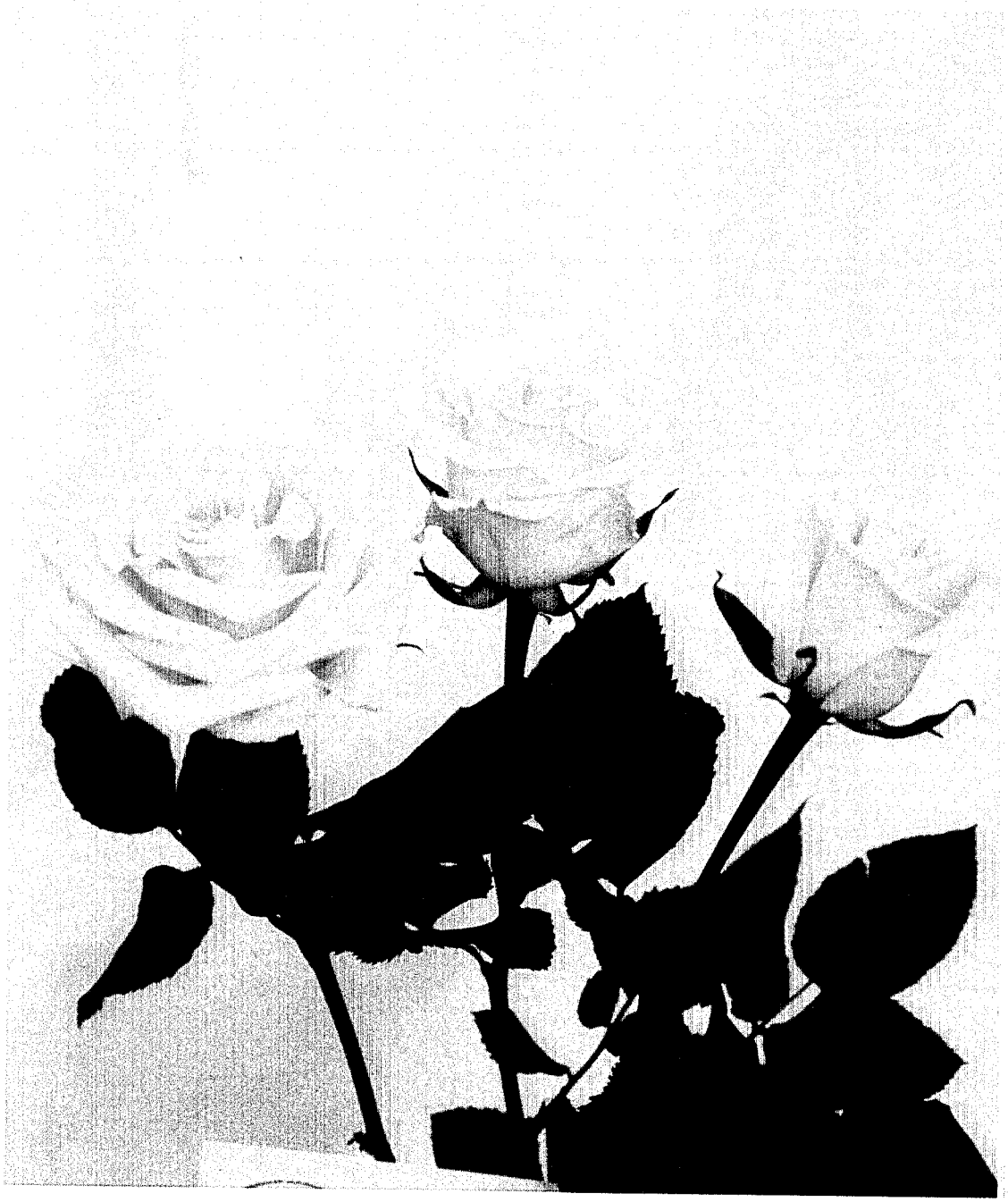

* * * * *